(12) United States Patent
Hufford et al.

(10) Patent No.: US 12,408,996 B2
(45) Date of Patent: Sep. 9, 2025

(54) DISPLAYING SUTURE FORCE INFORMATION IN SURGERY

(71) Applicant: Asensus Surgical US, Inc., Durham, NC (US)

(72) Inventors: Kevin Andrew Hufford, Durham, NC (US); Caleb T. Osborne, Durham, NC (US)

(73) Assignee: Asensus Surgical US, Inc., Durham, NC (US)

( * ) Notice: Subject to any disclaimer, the term of this patent is extended or adjusted under 35 U.S.C. 154(b) by 15 days.

(21) Appl. No.: 17/679,032

(22) Filed: Feb. 23, 2022

(65) Prior Publication Data

US 2022/0265372 A1 Aug. 25, 2022

Related U.S. Application Data

(60) Provisional application No. 63/152,834, filed on Feb. 23, 2021.

(51) Int. Cl.
| | |
|---|---|
| *A61B 34/30* | (2016.01) |
| *A61B 17/062* | (2006.01) |
| *A61B 34/00* | (2016.01) |
| *G06T 19/00* | (2011.01) |
| *A61B 17/00* | (2006.01) |
| *A61B 90/00* | (2016.01) |

(52) U.S. Cl.
CPC ............ *A61B 34/25* (2016.02); *A61B 17/062* (2013.01); *A61B 34/30* (2016.02); *G06T 19/006* (2013.01); *A61B 2017/00075* (2013.01); *A61B 2017/00212* (2013.01); *A61B 2034/254* (2016.02); *A61B 2090/061* (2016.02); *A61B 2090/064* (2016.02)

(58) Field of Classification Search
None
See application file for complete search history.

(56) References Cited

U.S. PATENT DOCUMENTS

| | | | |
|---|---|---|---|
| 9,155,544 B2 * | 10/2015 | Bonutti | A61B 17/8852 |
| 9,901,401 B2 | 2/2018 | Yoon | |
| 10,285,765 B2 | 5/2019 | Sachs et al. | |
| 2008/0108873 A1 | 5/2008 | Gattani et al. | |
| 2009/0248038 A1 * | 10/2009 | Blumenkranz | A61B 34/30 |
| | | | 606/130 |
| 2011/0319932 A1 * | 12/2011 | Avelar | A61B 90/90 |
| | | | 606/228 |
| 2019/0192259 A1 * | 6/2019 | Kopelman | A61B 5/682 |
| 2019/0275323 A1 * | 9/2019 | Castleberry | A61B 18/10 |
| 2023/0015516 A1 * | 1/2023 | Meglan | A61B 17/0469 |

FOREIGN PATENT DOCUMENTS

| | | |
|---|---|---|
| WO | 2013132501 A1 | 9/2013 |
| WO | 2017098503 A1 | 6/2017 |
| WO | 2017098507 A1 | 6/2017 |

\* cited by examiner

*Primary Examiner* — Joni Hsu

(57) ABSTRACT

In a system and method conveying suture force information in surgery, real times images of a surgical site are captured and displayed on a display. A suture is engaged using at least one surgical instrument, which in some cases is a robotic surgical instrument. The system determines a tension in the suture using force data obtained from force sensors associated with the instrument or a robotic manipulator used to manipulate the instrument, or using computer vision techniques applied to the captured images. An overlay is generated and displayed on the display depicting the determined tension.

16 Claims, 9 Drawing Sheets

DISPLAYING SUTURE FORCE INFORMATION IN SURGERY

This application claims the benefit of U.S. Provisional Application No. 63/152,834, filed Feb. 23, 2021, which is incorporated herein by reference.

BACKGROUND

In robot-assisted surgical procedures, instruments are moved by robotic manipulators according to instructions from a surgeon giving input using one or more input devices.

Some surgical systems, such as the Senhance System marketed by Asensus Surgical, Inc., generate haptic (force and tactile) feedback to the input device being manipulated by the user, providing the surgeon with useful information about forces experienced by the instruments within the body.

In some contexts, it may be desirable to give the surgeon additional or alternate means of feedback on forces to a surgeon. To prevent damage to fragile tissue, or to prevent events such as suture breakage, the ability to convey to the user the amount of force that is being applied by the surgical instruments to the user is particularly beneficial. This may augment haptics, or provide similar information if haptics is unavailable. This may also provide different fidelity of force information than that provided by haptics—either fine-resolution feedback in some cases, or more qualitative/gross feedback if certain thresholds are crossed.

This application describes systems and methods that provide visual feedback to a user representing forces applied to a suture using a robotically controlled surgical instrument.

BRIEF DESCRIPTION OF THE DRAWINGS

FIGS. 8A-8C and FIGS. 9A-9B are similar to the prior figures, but show still other ways to graphically convey force information.

DETAILED DESCRIPTION

Figure 1:
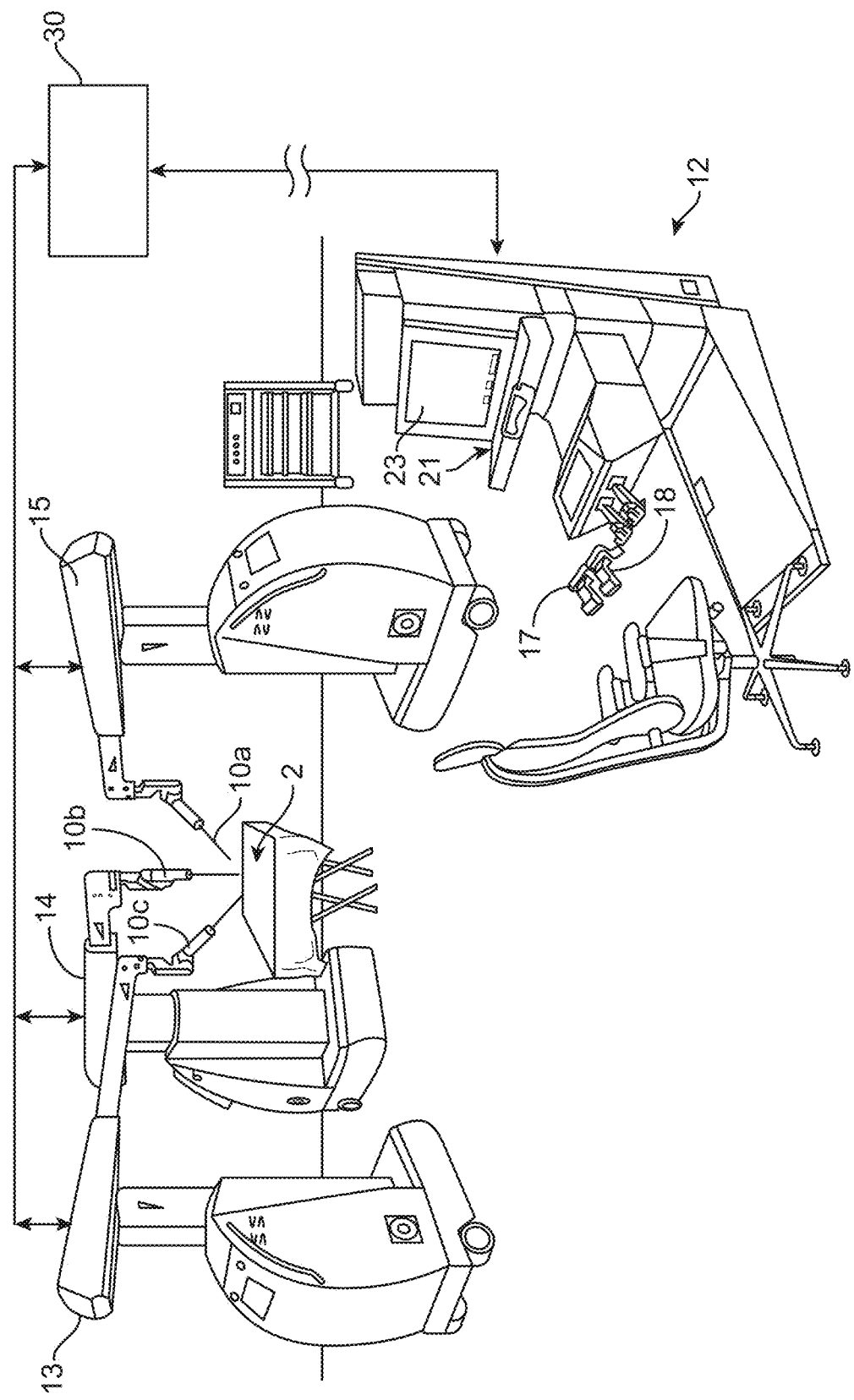
FIG. 1 shows an example of a robot-assisted surgical system.

Although the inventions described herein may be used on a variety of robotic surgical systems, the embodiments will be described with reference to a system of the type shown in FIG. 1. In the illustrated system, a surgeon console 12 has two input devices such as handles 17, 18. The input devices 12 are configured to be manipulated by a user to generate signals that are used to command motion of a robotically controlled device in multiple degrees of freedom. In use, the user selectively assigns the two handles 17, 18 to two of the robotic manipulators 13, 14, 15, allowing surgeon control of two of the surgical instruments 10a, 10b, and 10c disposed at the working site at any given time. To control a third one of the instruments disposed at the working site, one of the two handles 17, 18 is operatively disengaged from one of the initial two instruments and then operatively paired with the third instrument. A fourth robotic manipulator, not shown in FIG. 1, may be optionally provided to support and maneuver an additional instrument.

One of the instruments 10a, 10b, 10c is a camera that captures images of the operative field in the body cavity. The camera may be moved by its corresponding robotic manipulator using input from a variety of types of input devices, including, without limitation, one of the handles 17, 18, additional controls on the console, a foot pedal, an eye tracker 21, voice controller, etc. The console may also include a display or monitor 23 configured to display the images captured by the camera, and for optionally displaying system information, patient information, etc.

A control unit 30 is operationally connected to the robotic arms and to the user interface. The control unit receives user input from the input devices corresponding to the desired movement of the surgical instruments, and the robotic arms are caused to manipulate the surgical instruments accordingly.

The input devices 17, 18 are configured to be manipulated by a user to generate signals that are processed by the system to generate instructions used to command motion of the manipulators in order to move the instruments in multiple degrees of freedom.

One or more of the degrees of freedom of the input devices are coupled with an electromechanical system capable of providing tactile haptic feedback to the surgeon, and optionally providing gravity compensation for the user input, and/or. It should be understood that the concepts described in this application are not limited to any particular user input device configuration.

Sensor configurations by which forces experienced by a surgical instrument may be sensed or derived are described in U.S. Pat. No. 9,707,684 ("Force Estimation in a Minimally Invasive Robotic Surgery System") and US Application No. 2019-0060019 ("Force Estimation Using Robotic Manipulator Force Torque Sensors"), each of which is incorporated herein by reference. U.S. Pat. No. 9,707,684 describes a surgical system having a robot manipulator arm, that has an effector unit equipped with a six degrees-of-freedom (6-DOF or 6-axes) force/torque sensor. The effector unit is configured for holding a minimally invasive surgical instrument which is removably mounted thereto. US Application No. 2019-0060019 describes a robotic manipulator arm to which a surgical instrument is removably mounted for use in surgery. It describes that forces may be determined by angular position sensors and/or torque sensors positioned at multiple joints of the robotic manipulator arm. In other embodiments of the presently disclosed methods, forces applied by the instruments may also be sensed or derived using input from force sensors in or on the surgical instrument, such as on the instrument shaft.

In preferred configurations, one or more force sensors are positioned to obtain force data corresponding to forces experienced by each of the surgical instruments for which force information is desired.

Figure 2:
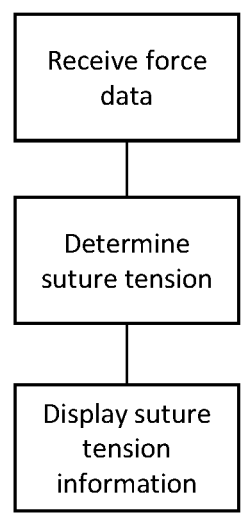
FIG. 2 is a block diagram illustrates steps of a method for displaying suture force information.

In a system incorporating aspects of the described invention, the system includes at least one processor of the system (such as one forming part of the control unit). The at least one processor includes memory storing instructions executable by the processor to receive force data from one or more force sensors associated with a surgical instrument or from other sources, determine using that force data the amount of tension applied to a suture engaged by that surgical instrument, and to generate a display visual feedback communicating the tension to the user, preferably as an overlay on the image display 23 that also displays the endoscopic image from the camera. See FIG. 2. Various types of visual feedback are described below. Note that a suture is considered "engaged" by a surgical instrument, as that term is used herein, when the surgical instrument is applying force in any way to that suture, regardless of whether the suture (or a needle carrying the suture) is grasped within the jaws of the surgical instrument. For example, a suture is considered engaged by a surgical instrument when the shaft of the instrument is moved laterally against the suture to alter the tension on the suture.

The suture tension may be displayed using any type of overlay that visually conveys the force information. As a simple example, the numerical force itself may be displayed in units familiar to the user. It may, however, be helpful to the user to convey the information with reference to a predetermined optimal force and/or a predetermined maximal force. For example, where the numerical force is displayed, the color in which the digits are shown may change depending on the level of the force. For example, very low forces may be displayed using light colored or white text, which changes to green when forces are within a predetermined target or optimal range. Forces exceeding the optimal level or range might be displayed as orange, and then red as they well exceed the target level/range or approach a predetermined maximum.

In other embodiments, the force information is graphically depicted in addition to, or as an alternative to, the numerical display.

Figure 3A:
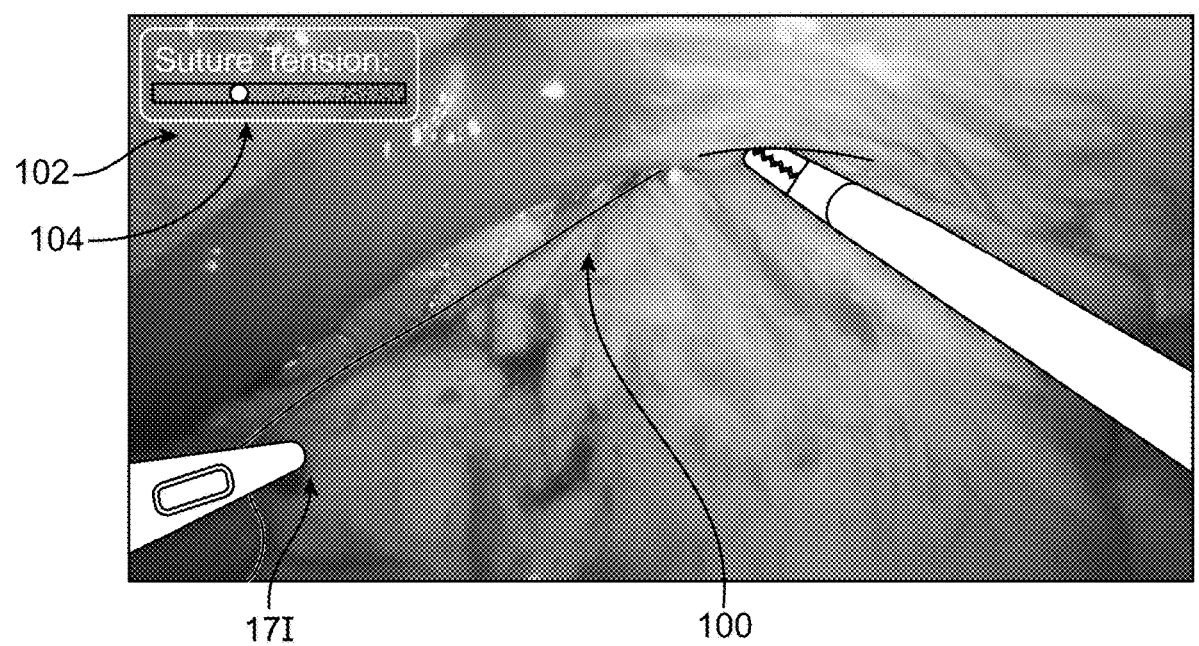
FIGS. 3A-3C illustrate an image display on which a real time camera image of a surgical procedure is displayed, and on which force information is graphically displayed according to a first embodiment.
Figure 3B:
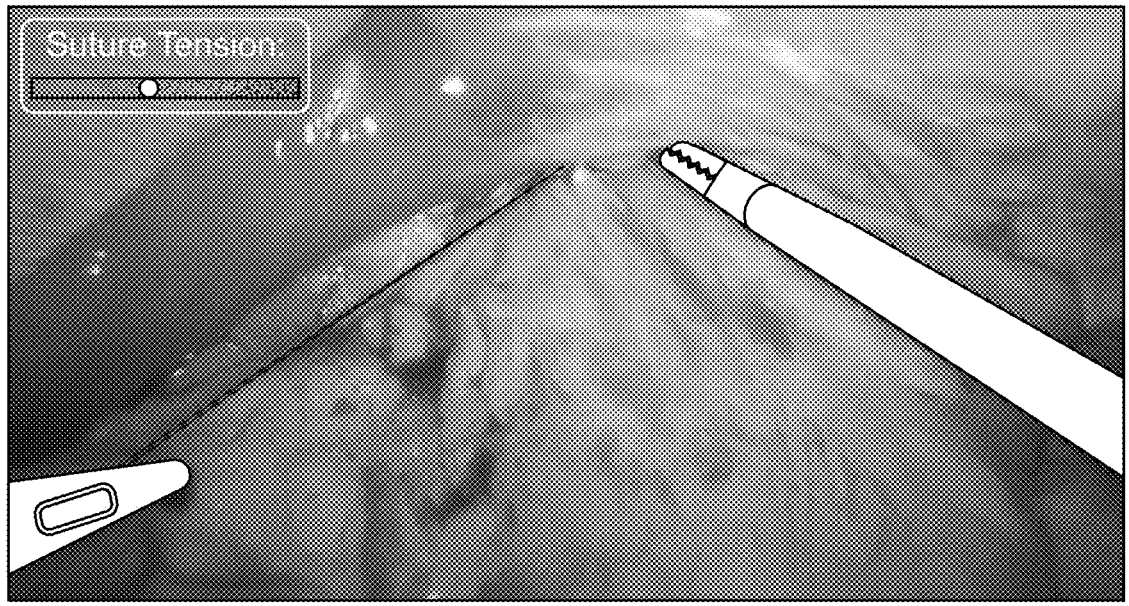
Figure 3C:
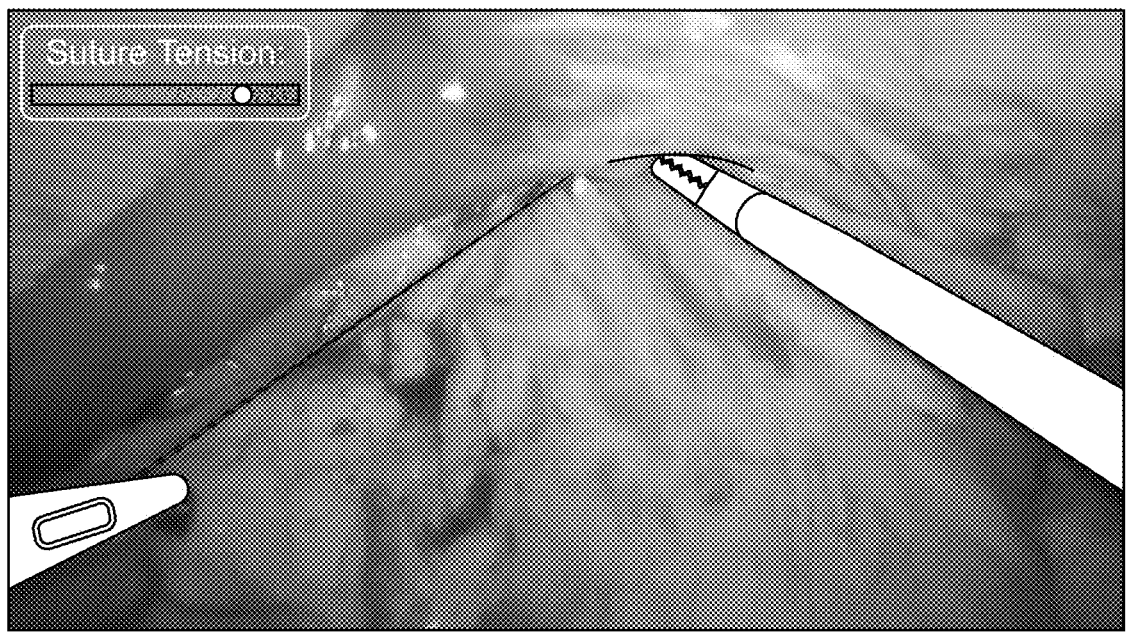

Referring to FIGS. 3A-3C, an image display from the real time endoscopic view is shown, with surgical instruments disposed at the surgical site. The instrument 17l visible on the left is grasping a length of suture 100. In this embodiment, suture tension is displayed using a fixed graphic 102 with an icon 104 that moves relative to the fixed graphic to depict the level of tension. In this embodiment, the fixed graphic 102 is a linear graphic designed so that the icon 104 is positioned towards the left of the graphic to represent lower forces, and towards the right of the graphic to represent higher forces. The linear graphic may be a color bar, with color changing from left to right along the bar, to depict increasing levels of force. Various colors may be used, but in the illustrated embodiment the colors used are white or another light color at the left (corresponding to light forces), shades of green towards the mid-regions (corresponding to forces within a predetermined optimal range), then yellow, orange and red (for forces exceeding the optimal level). Note that in any of the embodiments in which color is used, alternative representations of force may be shown, such as words describing the force (e.g. "low," "target," "high") instead of, or in addition to, the color.

As shown in FIGS. 3B and 3C, the icon 104 moves right relative to the linear graphic as tension on the suture 100 increases, with the graphic showing tension in the target range (green) in FIG. 3B, and exceeding the target range (orange) in FIG. 3C.

Figure 4A:
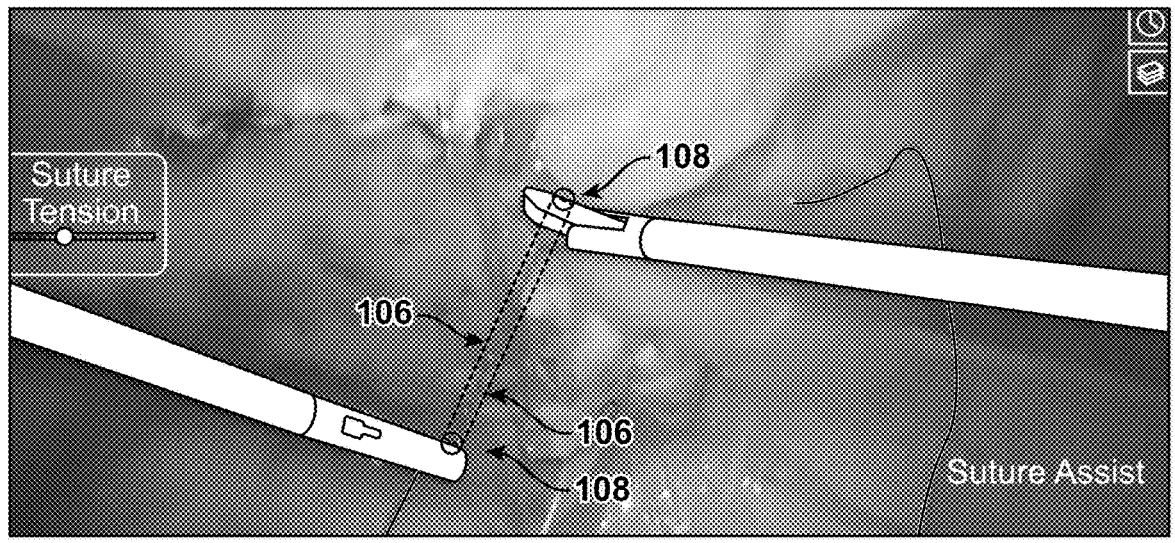
FIGS. 4A-4B are similar to FIGS. 3A-3C but further illustrate use of overlays to mark the sutures and suture segment end points.
Figure 4B:

The displays depicted in FIGS. 4A and 4B use a similar form of graphic to that shown in FIGS. 3A-3C, but they additionally highlight the suture itself, in this case using dashed lines 106 (shown in white) running parallel to the suture on opposite sides. The ends of the exposed segment of suture (i.e. the end engaged by the instrument and the end engaged to the tissue) are also marked using circles 108. In FIG. 4A, the depicted tension corresponds to the tension applied between two instruments. In FIG. 4B, a line of stitches has been placed in the tissue, and the depicted tension corresponds to the tension applied between an instrument and the portion of the suture engaged to the tissue.

The system may be pre-programmed using the target range and maximal permitted force, or the user may input them prior to or during the procedure. In some embodiments, the system may engage other mechanisms to alert the user as forces approach the maximal permitted forces, such as enhanced forces to the user at the haptic interface, alternative haptic feedback such as vibratory feedback. In some embodiments, the robotic system may be programmed so that when the maximal permitted force is reached, the robotic manipulator will not increase the forces applied to the suture even if commanded to do so at the user interface.

Figure 5A:
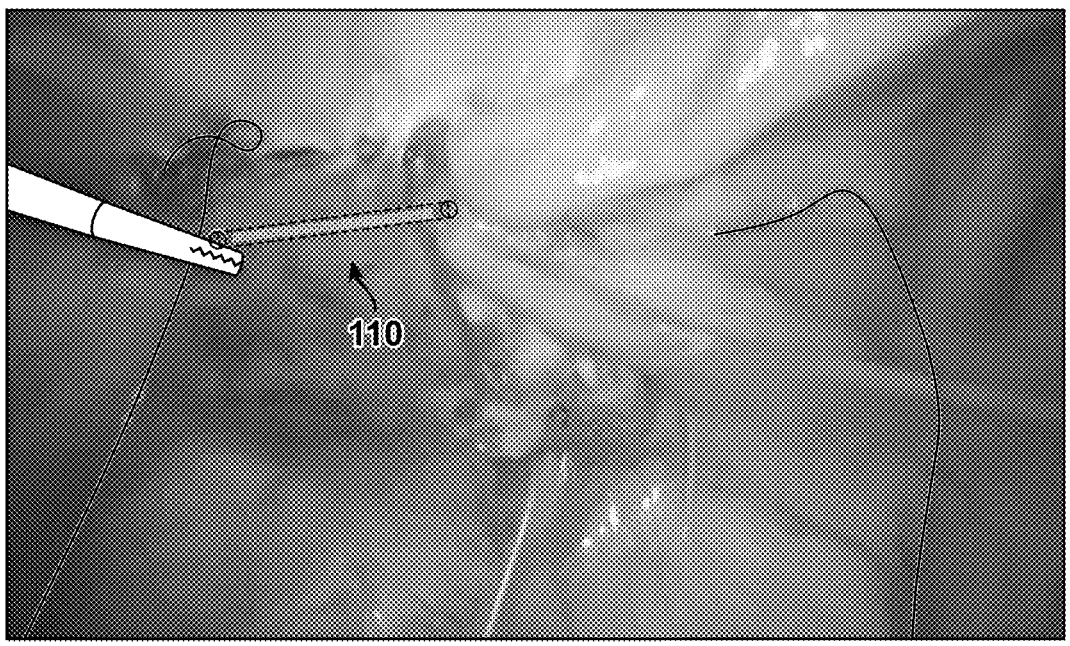
FIGS. 5A-5B are similar to the prior figures, but differ in that force information is graphically displayed according to a second embodiment.
Figure 5B:
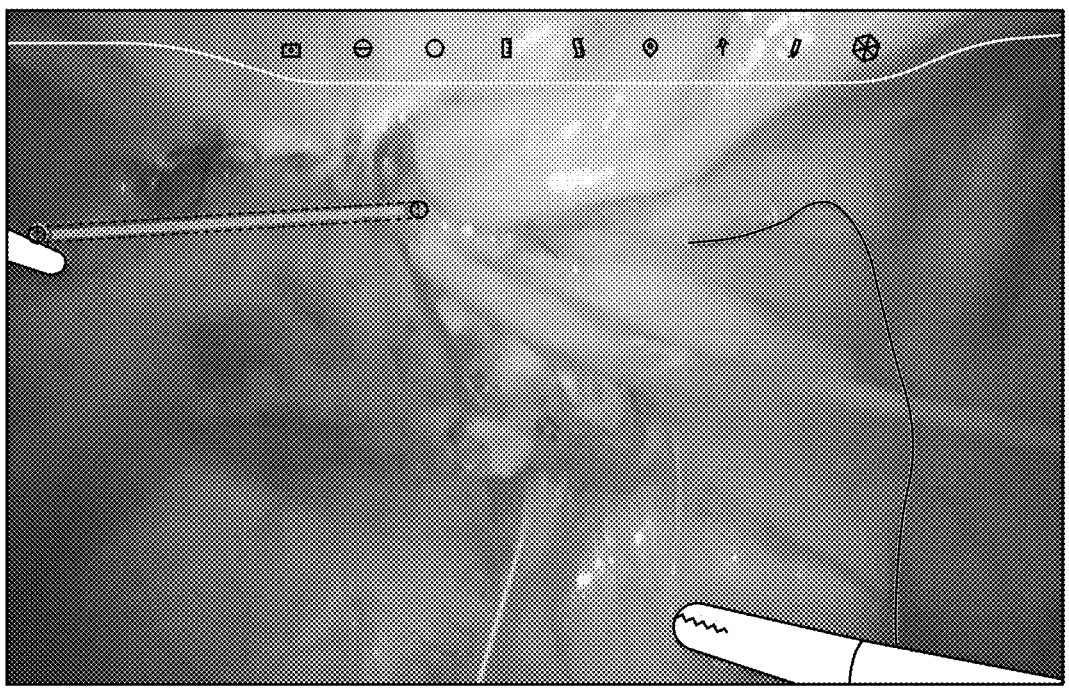

In the FIGS. 5A and 5B embodiment, color overlays 110 corresponding to the level of tension in the suture (relative to the target force or range) may be displayed on the exposed segment of suture to which the tension is being applied. In FIG. 5A that overlay is green, indicating tension at the optimal level or within the optimal range. In FIG. 5B it is orange, indicating tension beyond the optimal level or range. In a slight modification to this embodiment, the overlays might instead be displayed adjacent to the suture segment so as not to block it from the user's view.

In some embodiments, the overlay may be off/invisible if the tension is at a nominal level, and only appear if the tension/force rises above a threshold. The overlay/alert may then disappear as the tension/force again drops below a threshold.

Figure 6A:
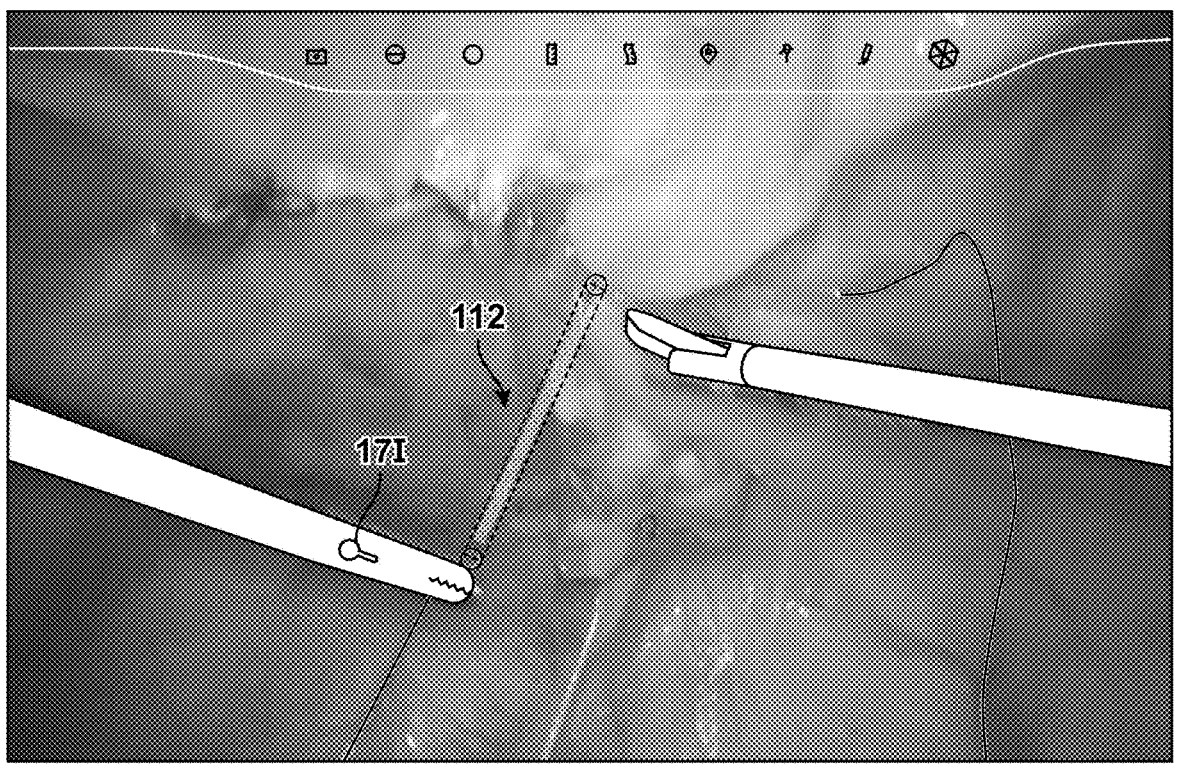
FIGS. 6A-6C illustrate an image display on which a real time camera image of a surgical procedure is displayed, and show a sequence of steps in which force information is graphically displayed for two suture segments.
Figure 6B:
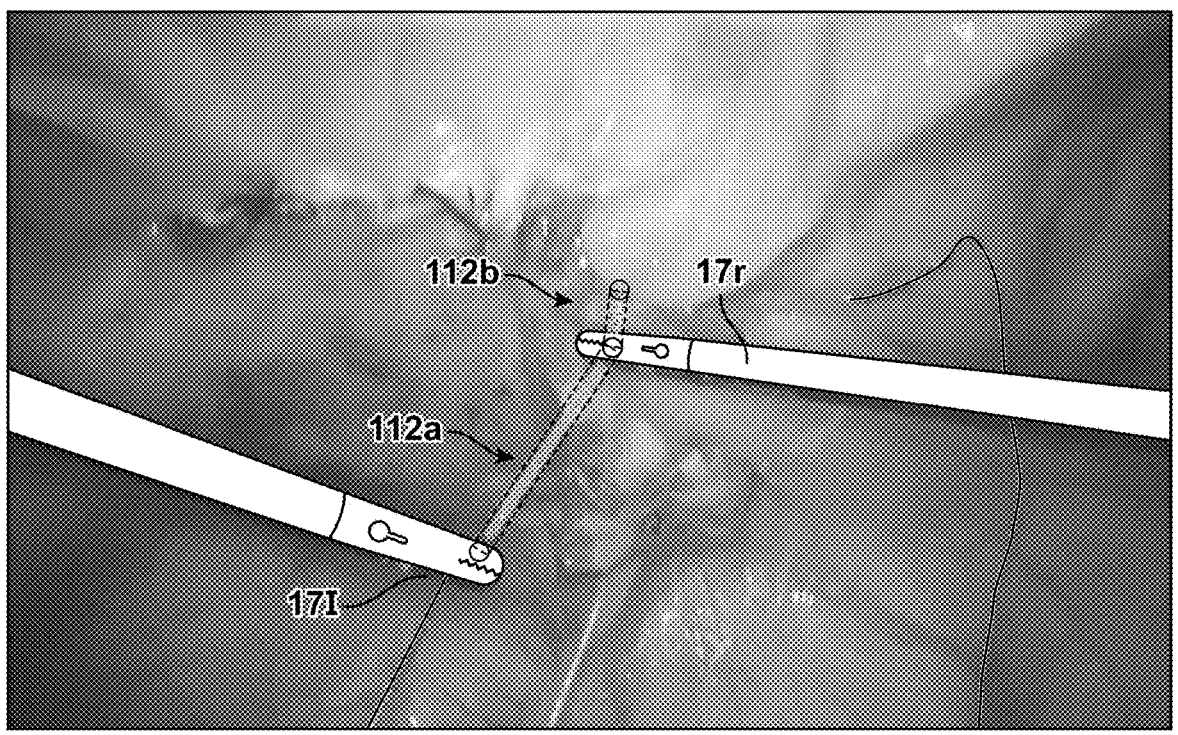
Figure 6C:
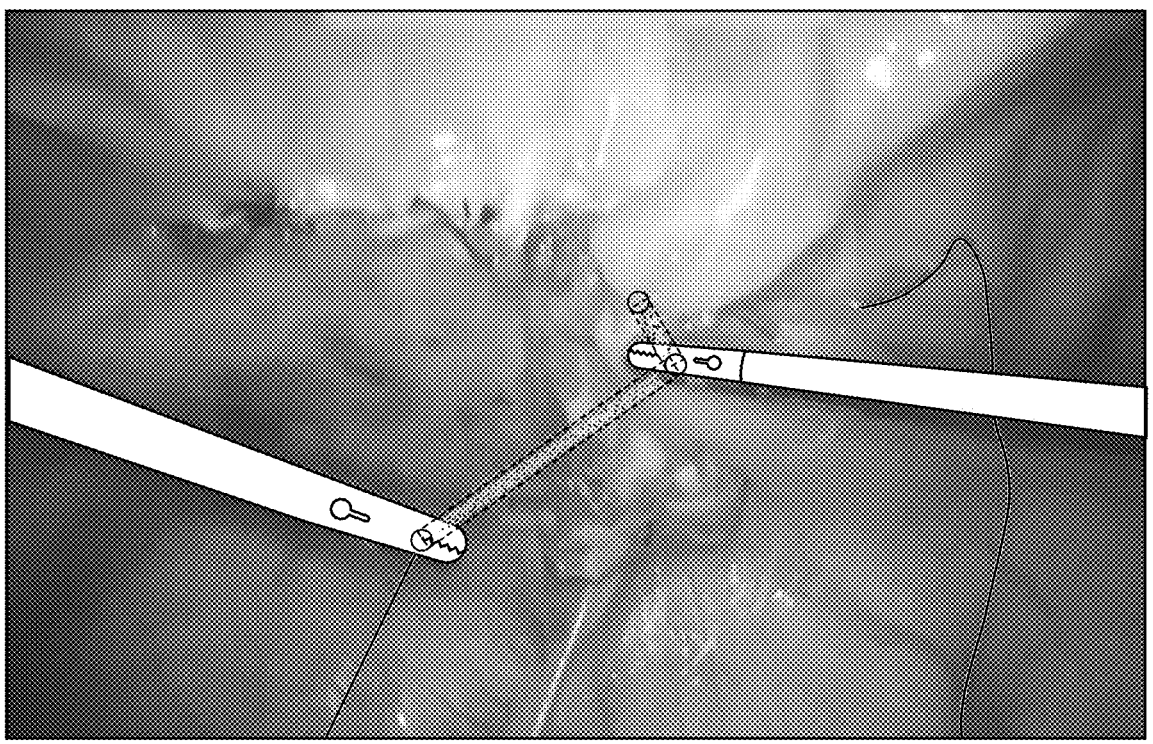

FIGS. 6A-6C show a sequence of steps illustrating that the system is capable of conveying force information for different exposed segments of suture. In FIG. 6A, the suture is engaged by instrument 17l, and a force overlay 112 in the form of a green bar is displayed over the length of suture running from the instrument to its engagement point at the tissue. In FIG. 6B, the suture continues to be engaged by instrument 17l, but is additionally engaged by instrument 17r near the tissue, creating an inflection point in the suture, resulting in two segments in the exposed length of segment. Depending on the forces applied by each of the instruments 17l, 17r, the tension in each of these segments may be different. The system calculates the forces in each segment using data from the force sensors associated with each of the instruments 17l, 17r and displays force information for each suture segment. In FIG. 6B, the segment towards the left has a green overlay 112a, and the short segment towards the right has an orange overlay 112b. In FIG. 6C, the tension on each segment has increased, and so overlay 112a on the left has changed to orange, while overlay 112b on the right has changed to red.

Figure 7A:
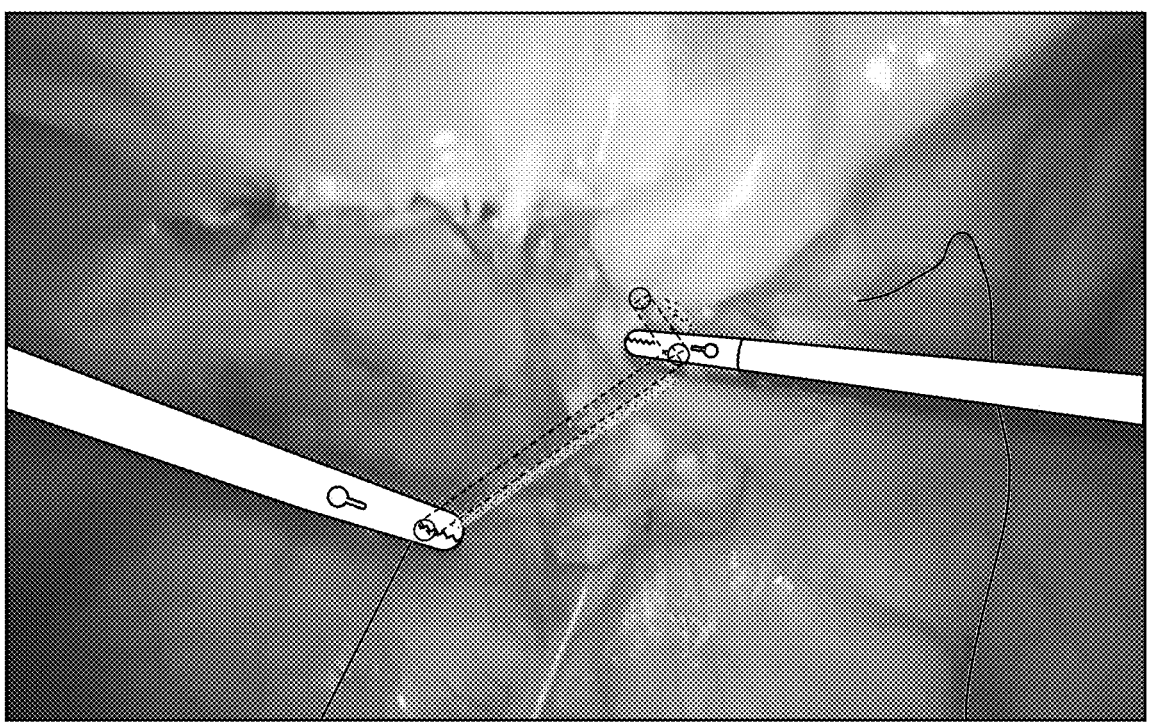
FIGS. 7A-7C are similar to FIG. 6C, but show alternate ways of displaying force information for the two suture segments.
Figure 7B:
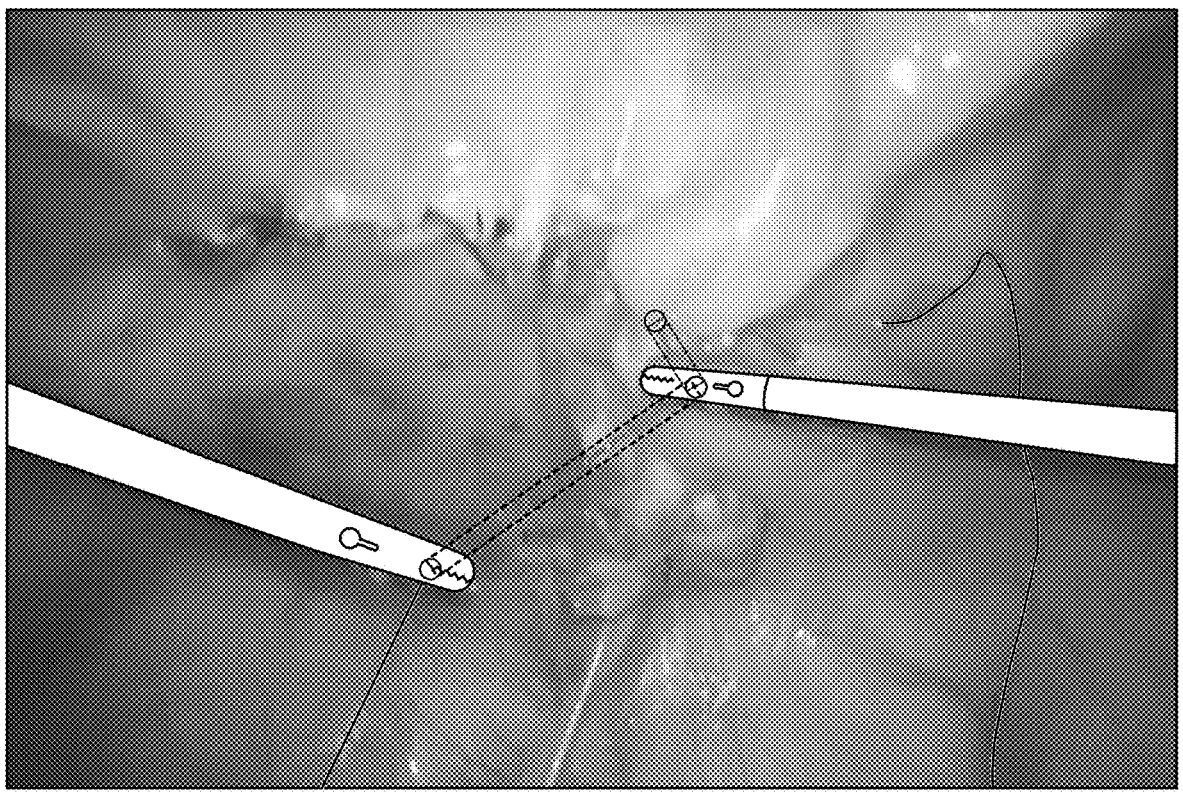
Figure 7C:
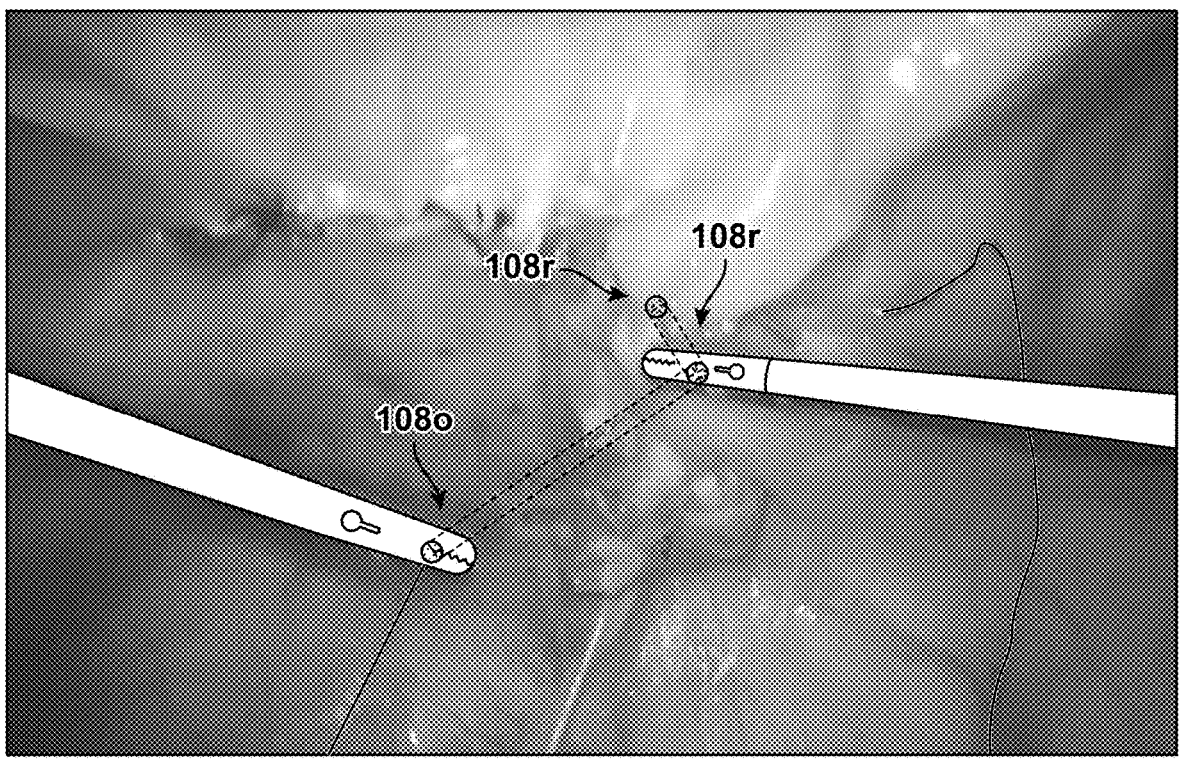

FIGS. 7A-7C all are similar to FIG. 6C, but show alternate ways of displaying the color overlay. In FIG. 7A, the color bars are shown adjacent to, rather than over, the suture segments. In FIG. 7B they are shown as parallel dashed lines on opposite sides of each suture segment. In FIG. 7C, the ends of each segment are marked using overlays 108o, 108r marking the ends of each segment (shown as dots) that are orange and red, respectively.

In the FIG. 8A-8C embodiment, alternative graphical overlays are used to convey force information, and may include a directional component. These figures show a force-conveying icon on an instrument shaft, which in this case is a circle that changes color depending on where the force applied by that instrument falls relative to the target force or range. The color of the circle changes as it crosses certain force thresholds. The size of the circle increases to convey increased force. A bar extending from the force-conveying icon has a length that increases to depict increased force on the shaft of the instrument.

In this case, the bar is used to convey the tension force on the instrument shaft, while the circle is conveying the jaw/grip force on the instrument tips. When pulling harder, a user will likely naturally grip harder as well to prevent slippage in the jaws, thus the diagrams show a proportional increase in both the instrument shaft force and grip force overlays.

In other implementations, there may be only one indicator which may show a cumulative/hybrid semi-quantitative calculation of force. In other implementations, either only grip force or only shaft force may be displayed. These options may be selectable by the user.

FIG. 9A shows an embodiment in which a force-conveying icon (here a colored circle) overlay may indicate the qualitative range of force, while a displayed number may indicate either an actual value of the force being applied, or some classification of the force level along a scale (e.g. 1-5). In FIG. 9B, a force-conveying icon (here a red circle) indicates that the jaw grip force is above a desired threshold. The bar extending from that icon indicates the direction of the applied force on the instrument shaft.

Circle or other marker may change size, shape, color, opacity, flashing pattern, or other similar means to convey the amount of force, its directionality, etc.

In other implementations, system information/alerts related to force or other types of status may be overlaid on the surgical view, instrument shafts, tips, or nearby them to present pertinent information in an area of visual focus for the user. An example of this may be an "exceeding force" error which affects the motion of the arm, and helps the user to more immediately address the issue.

While the primary system described above makes use of force sensor information to determine the forces/tensions, it should be understood that sources of force data may be used for that purpose. For example, computer vision techniques may be applied to real time images of the surgical site, such as those captured by the endoscopic camera. The computer vision algorithm may recognize any of the following and use them to determine forces:

Recognizing a taut suture vs a slack suture
Recognizing changes in the suture's shape or length
Recognizing distortions in tissue (e.g. 3D shape change) resulting from contact or engagement with the suture
Recognizing motion(s) of underlying tissue (even if the suture itself doesn't change shape)

It should be noted that even when force data is obtained from force sensors, computer vision may also be used to identify the suture in the field of view using real time image data, such as when the suture and/or the exposed endpoints of suture segments are to be marked using overlays, and to track the suture within the surgical site.

All patents and applications referenced herein, including for purposes of priority, are incorporated herein by reference.

What is claimed is:

1. A method of conveying suture force information in surgery, comprising:
    capturing real time images of a surgical site;
    displaying the real time images on a display;
    providing a robotic manipulator arm, an end effector at a distal end of the robotic manipulator arm, the end effector including a force sensor,
    removably mounting a surgical instrument to the robotic manipulator arm;
    positioning a distal end of the surgical instrument at the surgical site;
    using the robotic manipulator arm, maneuvering the surgical instrument to apply a suture to tissue at the surgical site using the surgical instrument and to apply force to the suture that has been applied to the tissue;
    receiving force data from the force sensor,
    based on the force data, determining a tension in the suture resulting from application of force to the suture by the surgical instrument; and
    displaying an overlay on the display depicting the determined tension.

2. The method of claim 1, wherein the method further includes applying computer vision to the real time images to recognize an exposed segment of the suture, and displaying an overlay identifying the suture.

3. The method of claim 2, wherein displaying an overlay on the display depicting the determined tension includes displaying an overlay highlighting the exposed segment of the suture in a color selected to convey whether the determined tension is below or above the predetermined target range or value.

4. The method of claim 1, wherein the method further includes applying computer vision to the real time images to recognize an exposed segment of the suture, and displaying an overlay identifying the ends of the exposed segment.

5. The method of claim 1, wherein the overlay depicts the amount of determined tension relative to a predetermined target range or value.

6. The method of claim 5, wherein displaying an overlay on the display depicting the determined tension includes displaying an overlay showing a numerical value of the determined tension in a color selected to convey whether the predetermined tension is below or above the predetermined target range or value.

7. The method of claim 1, wherein displaying an overlay on the display depicting the determined tension includes displaying an overlay showing a numerical value of the determined tension.

8. The method of claim 1, wherein displaying an overlay on the display depicting the determined tension includes displaying an overlay comprising a first, fixed, graphic and a second graphic moveable relative to the first graphic to depict increases or decreases in the determined tension.

9. A method of conveying suture force information in surgery, comprising:
    capturing real time images of a surgical site;
    displaying the real time images on a display;
    providing a robotic manipulator having a plurality of joints, each including a force sensor;
    removably mounting a surgical instrument to the robotic manipulator arm;
    positioning a distal end of the surgical instrument at the surgical site;
    using the robotic manipulator arm, maneuvering the surgical instrument to apply a suture to tissue at the surgical site using the surgical instrument and to apply force to the suture that has been applied to the tissue;
    receiving force data from the force sensors, based on the force data, determining a tension in the suture resulting from application of force to the suture by the surgical instrument; and displaying an overlay on the display depicting the determined tension.

10. The method of claim 9, wherein the method further includes applying computer vision to the real time images to recognize an exposed segment of the suture, and displaying an overlay identifying the suture.

11. The method of claim 10, wherein displaying an overlay on the display depicting the determined tension includes displaying an overlay highlighting the exposed segment of the suture in a color selected to convey whether the determined tension is below or above the predetermined target range or value.

12. The method of claim 9, wherein the method further includes applying computer vision to the real time images to recognize an exposed segment of the suture, and displaying an overlay identifying the ends of the exposed segment.

13. The method of claim 9, wherein the overlay depicts the amount of determined tension relative to a predetermined target range or value.

14. The method of claim 13, wherein displaying an overlay on the display depicting the determined tension includes displaying an overlay showing a numerical value of the determined tension in a color selected to convey whether the predetermined tension is below or above the predetermined target range or value.

15. The method of claim 9, wherein displaying an overlay on the display depicting the determined tension includes displaying an overlay showing a numerical value of the determined tension.

16. The method of claim 9, wherein displaying an overlay on the display depicting the determined tension includes displaying an overlay comprising a first, fixed, graphic and a second graphic moveable relative to the first graphic to depict increases or decreases in the determined tension.

* * * * *